United States Patent [19]

Latimer et al.

[11] Patent Number: 5,125,272
[45] Date of Patent: Jun. 30, 1992

[54] ULTRASONIC CRACK SIZING METHOD

[75] Inventors: Paul J. Latimer; Hubert L. Whaley, both of Lynchburg, Va.

[73] Assignee: The Babcock & Wilcox Company, New Orleans, La.

[21] Appl. No.: 324,484

[22] Filed: Mar. 16, 1989

[51] Int. Cl.⁵ .......................................... G01N 29/04
[52] U.S. Cl. .................................................. 73/598
[58] Field of Search ............... 73/592, 598, 600, 602, 73/614, 615, 620, 628

[56] References Cited

U.S. PATENT DOCUMENTS

| | | | |
|---|---|---|---|
| 4,274,288 | 6/1981 | Tittmann et al. | 73/602 |
| 4,522,064 | 6/1985 | McMillan | 73/628 |
| 4,658,649 | 4/1987 | Brook | 73/598 |

FOREIGN PATENT DOCUMENTS

| | | | |
|---|---|---|---|
| 0228345 | 10/1986 | Japan | 73/598 |

OTHER PUBLICATIONS

Achenbach, J. D., *Wave Propagation in Elastic Solids*, North Holland Publishing Co., 1973.
EPRI, *U.-T. Operator Training for Planar Flaw Sizing*, EPRI Nondestructive Evaluation Center, 1300 Harris Blvd., P.O. Box 217097, Charlotte, N.C. 28221, Aug. 1984.

*Primary Examiner*—Louis M. Arana
*Attorney, Agent, or Firm*—Vytas R. Matas; Robert J. Edwards; Daniel S. Kalka

[57] ABSTRACT

An ultrasonic tip diffraction technique for determining the depth of a surface-opening crack is disclosed. Longitudinal ultrasonic waves are transmitted parallel to and along the crack and measurement of the time of travel of the waves diffracted at the tip of the crack is employed to determine the depth of the crack.

3 Claims, 6 Drawing Sheets

ULTRASONIC CRACK SIZING METHOD

BACKGROUND OF THE INVENTION

This invention relates to ultrasonic examination of surface discontinuities and, more particularly, to an ultrasonic tip diffraction technique for determining the depths of surface cracks.

The problem of determining so-called through-wall crack depths is one of the most difficult and important problems in nondestructive examination (NDE) today. It is particularly important in determining the integrity and remaining lifetime of a component.

Such surface breaking cracks have been sized by various NDE techniques including eddy current, ultrasonic surface waves and electrical potential methods.

Various ultrasonic and non-ultrasonic techniques are known for detecting or measuring flaws. The most common method of sizing is based on a measurement of echo amplitude after the ultrasound is reflected by the surface area of the crack. Examples of prior techniques are found in U.S. Pat. No. 4,679,437, U.S. Pat. No. 4,559,825, U.S. Pat. No. 4,289,033, U.S. Pat. No. 3,924,453, U.S. Pat. No. 3,349,607, U.S. Pat. No. 4,523,468, U.S. Pat. No. 4,467,654 and U.S. Pat. No. 2,725,491. All use angle beam shear waves for ultrasonic examination. U.S. Pat. No. 2,725,491 is primarily directed to an adjustable mounting adapter, as is U.S. Pat. No. 4,117,733. U.S. Pat. No. 4,612,808 describes a probe holder for use on irregular surfaces. U.S. Pat. No. 4,213,183, U.S. Pat. No. 4,052,889 and U.S. Pat. No. 4,393,711 are all based on adaptive learning techniques, which rely upon computer processing and combining of features selected from the ultrasonic signal and transformations of these signals. The system of U.S. Pat. No. 3,981,184 also uses computer processing to correlate ultrasonic indications with the coordinates of their sources and to discriminate between ultrasonic signals of different amplitudes.

U.S. Pat. No. 3,583,211 describes a method to ascertain that ultrasound has reached the entry surface at the correct angle to generate the desired angle beam wave. In U.S. Pat. No. 4,441,369, cracks with rough faceted surfaces are sized by determining locations of all facets, including those at the boundaries of the defect. U.S. Pat. No. 4,274,288 is directed to the use of surface wave interference to determine depth. The surface wave is scattered by the crack. U.S. Pat. No. 4,685,334 detects distributed hydrogen damage by measurement of increased attenuation and does not apply to either detection or sizing of discrete defects. U.S. Pat. No. 4,297,885 does not use ultrasonic methods but employs the detection of elastic energy released as cracks propagate to identify the presence of cracking. U.S. Pat. No. 4,448,080 describes a method for detecting cracks by the change in pressure of a medium pumped into a hole intersecting the crack.

In U.S. Pat. No. 4,475,394, an automated system for correlating particular ultrasonic echoes with specific defects is used. The correlation depends upon comparing probe motion to propagation distance change, keeping in mind the limited beam spread of the transducer. With signal amplitude variation with probe .position known for each defect, the size is determined from the transducer positions giving a preset minimum amplitude.

Ultrasonic tip diffraction is one of the most recently developed techniques for accurately sizing cracks. None of the aforementioned patents employ so-called tip diffracted signals in connection with the various aspects of inspection disclosed in those patents.

Two patents, U.S. Pat. No. 4,570,487 and U.S. Pat. No. 4,522,064, relate to defect sizing using tip diffracted techniques. In both cases, angle beam ultrasonic waves are used. Differences in arrival time of crack root and crack tip signals are used to determine crack size.

The methods previously described for measuring the depths of surface cracks are seriously limited by many physical and geometrical conditions. Restrictions on access creates a need to be able to size cracks in many different types of geometrical configurations that prevent the application of currently available techniques. In addition, many of the current sizing techniques described in the literature are very complex and would be difficult to apply in situations outside the laboratory. In no known case, has a technique been described that utilizes longitudinal waves that are along and parallel to the crack.

SUMMARY OF THE INVENTION

Longitudinal ultrasonic waves, in accordance with the present invention, are introduced through the surface at which the crack originated in a manner such that the longitudinal ultrasonic waves propagate parallel to the plane of the crack from the root to the- tip. It has been found that a portion of the tip diffracted signal returns after diffraction. Such weak, diffracted pulses have been found to be three or more orders of magnitude smaller than typical specularly reflected flaw signals. The waves diffracted directly back along the crack are used to determine the depth of the crack.

According to a preferred embodiment of the invention, the ultrasonic waves are introduced into a solid containing crack with a direct (contact) coupled transducer for example. When the ultrasonic wave reaches the end of the crack, a very small amplitude echo is produced at the boundary while most of the energy continues in the forward direction. Based on the measured arrival time of the echo back at the transducer and the known velocity of the ultrasonic waves in the solid, the depth of the crack can be determined. If the crack is not perpendicular to the surface, the measured crack depth will be the projection of the actual crack depth to a normal to the surface.

The parallel compressional wave method for sizing is much simpler both in principle and in practice than the other techniques now currently in use. This technique enables crack depths to be determined in certain geometrical configurations which were previously inaccessible. The crack depths can be read directly from the calibrated screen on an ultrasonic instrument. The measurements of crack depth can be made rapidly, and is not confined to the laboratory. It has many practical applications in the field.

Crack depth can advantageously be measured in accordance with the inventive technique whether the crack is empty or filled with a corrosion product or some other solid or liquid that has acoustic properties differing from the host medium. This property results from the fact that the signal used for measurement is the fast compressional wave that is coupled to the metal (or to the host medium). This signal arrives before the other competing signals and therefore can be easily identified.

The various features of novelty which characterize the invention are pointed out with particularity in the claims annexed to and forming a part of this specification. For a better understanding of the invention, its operating advantages and specific objects attained by its use, reference should be made to the accompanying drawing and descriptive matter in which there is illustrated and described a preferred embodiment of the invention.

BRIEF DESCRIPTION OF THE DRAWINGS

In the accompanying drawings, forming a part of this specification, and in which reference numerals shown in the drawings designate like or corresponding parts throughout the same.

DETAILED DESCRIPTION

Figure 1:
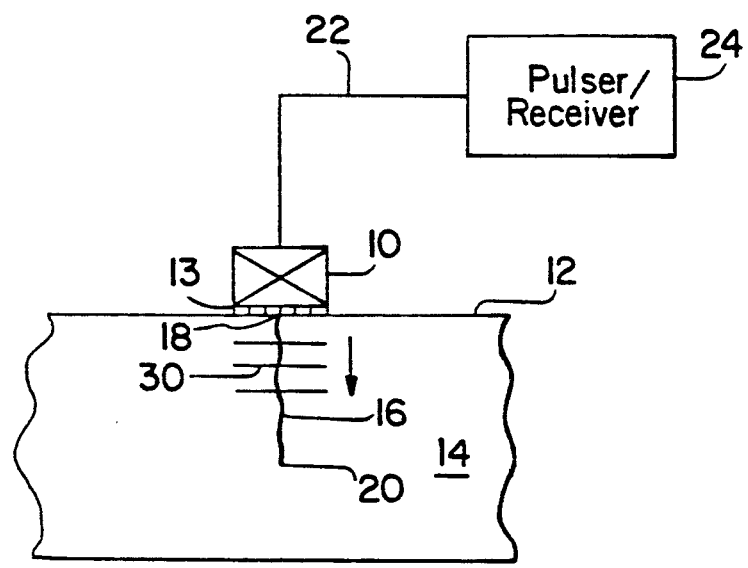
FIG. 1 illustrates a schematic side section view of a metallic specimen, such as a boiler tube, having a crack emanating into the specimen from a surface thereof, with a transmitting and receiving transducer mounted on the surface to carry out the method of the invention.

FIG. 1 shows an ultrasonic transducer 10 mounted on a surface 12 of specimen 14. A crack 16 extends between a root 18 of the crack opening at the surface 12 to a tip 20 located within the specimen 14 beneath the surface 12. To facilitate transmission of ultrasound into and out of the specimen, a couplant 13 is preferably used between the transducer 10 and the specimen 14.

The transducer 10 is electrically connected via line 22 to a pulser/receiver 24, comprising a pulser of a model KB-6000 pulser-receiver produced by Krautkramer-Branson Incorporated of Stratford, CT., and an MR 101 receiver produced by Metrotek Inc. of Richland, WA., to provide high voltage pulses having short pulse length and good damping, and to receive and amplify return pulses. In a preferred embodiment of the invention, a transducer produced by Panametrics of Waltham, MA. having a 0.25 inch diameter with a frequency of 20 MHz and a plastic delay line was employed.

As shown in FIG. 1, the transducer 10 is positioned in an orientation on the surface 12 for directing longitudinal ultrasonic waves through the surface 12 substantially normal to the surface and parallel to the crack 16. An ultrasonic signal is then generated and received by energizing the transducer 10 via the pulser/receiver 24.

The transducer 10 transmits longitudinal ultrasonic waves 30 at a predetermined frequency on the order of 10 to 50 MHz, through the material of the specimen parallel to the plane of the crack 16 from the root 18 to the tip 20.

Figure 2:
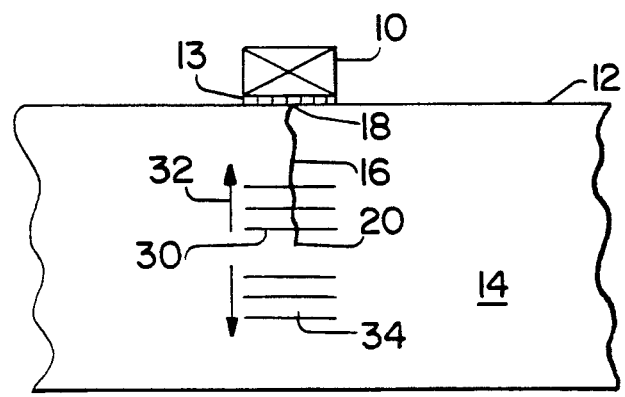
FIG. 2 is a schematic representation of the arrangement of FIG. 1 which illustrates the propagation of ultrasonic waves beyond the tip of the crack and the attendant reflection of the diffracted waves.
Figure 3:
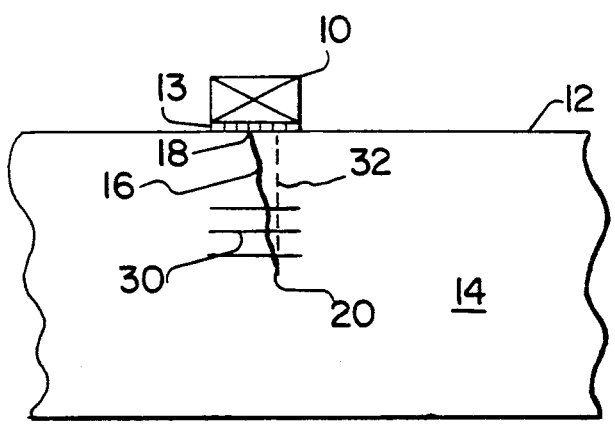
FIG. 3 is a schematic representation of an arrangement similar to FIG. 1 where in the crack is not perpendicular to the surface.

As shown in FIG. 2, when the ultrasonic waves 30 reach the tip end of the crack 16 a very small amplitude echo 32 is produced at the tip 20 while most of the ultrasonic energy 34 continues in the forward direction. By measuring the arrival time of the diffracted tip waves of echo 32 at the transducer 10, and knowing the velocity of the ultrasonic waves in the solid specimen, the depth of the crack can be determined. If the crack is not perpendicular to the surface, as shown in FIG. 3, the measured crack depth will be the projection of the actual crack length into a normal to the surface.

In practicing the invention as embodied here, the choice of transducer and pulser receiver was found to be critical. The ideal characteristics for this combination were a large narrow spike driving a highly damped transducer. The pulser which was found most suitable to deliver the high voltage spike was the KB-6130 pulser/preamplifier module for the KB-6000 ultrasonic test and data acquisition system.

The Panametrics transducers had a frequency of 20 MHz, a plastic delay line and an active element of 0.25 inches in diameter. For this application, the plastic delay that was supplied by the manufacturer was modified by machining the length to a minimum of approximately 0.10 inches. This smaller length substantially reduced the ultrasonic attenuation resulting from propagation in the plastic; however, the remaining length provided a good wear surface and damping for the piezoelectric crystal.

The recovery time of the instrumentation and the damping of the transducer set the lower limit for flaw depths that can be measured This lower limit was found to be approximately 50 mils (0.050 inches) for the particular pulser module and transducer used.

Although the KB-6000 was the only ultrasonic instrument found to be totally suitable for the application, it was necessary to remove the KB-6130 pulser module from the mainframe and repackage it in combination with a power supply interface circuit and Metrotek MR101 receiver. These steps were necessary because the physical dimensions of the KB-6000 mainframe were too large to allow it to be used in field applications such as inspecting the furnace wall of a black liquor recovery boiler.

The MR101 receiver is a wide band ultrasonic receiver that is designed to be used primarily in the 0.5 MHz to 20 MHz range. The receiver has a low noise input and a calibrated gain of up to 40 dB. The choice of receiver has not proven to be as crucial as the choice of pulser modules.

Figure 5:
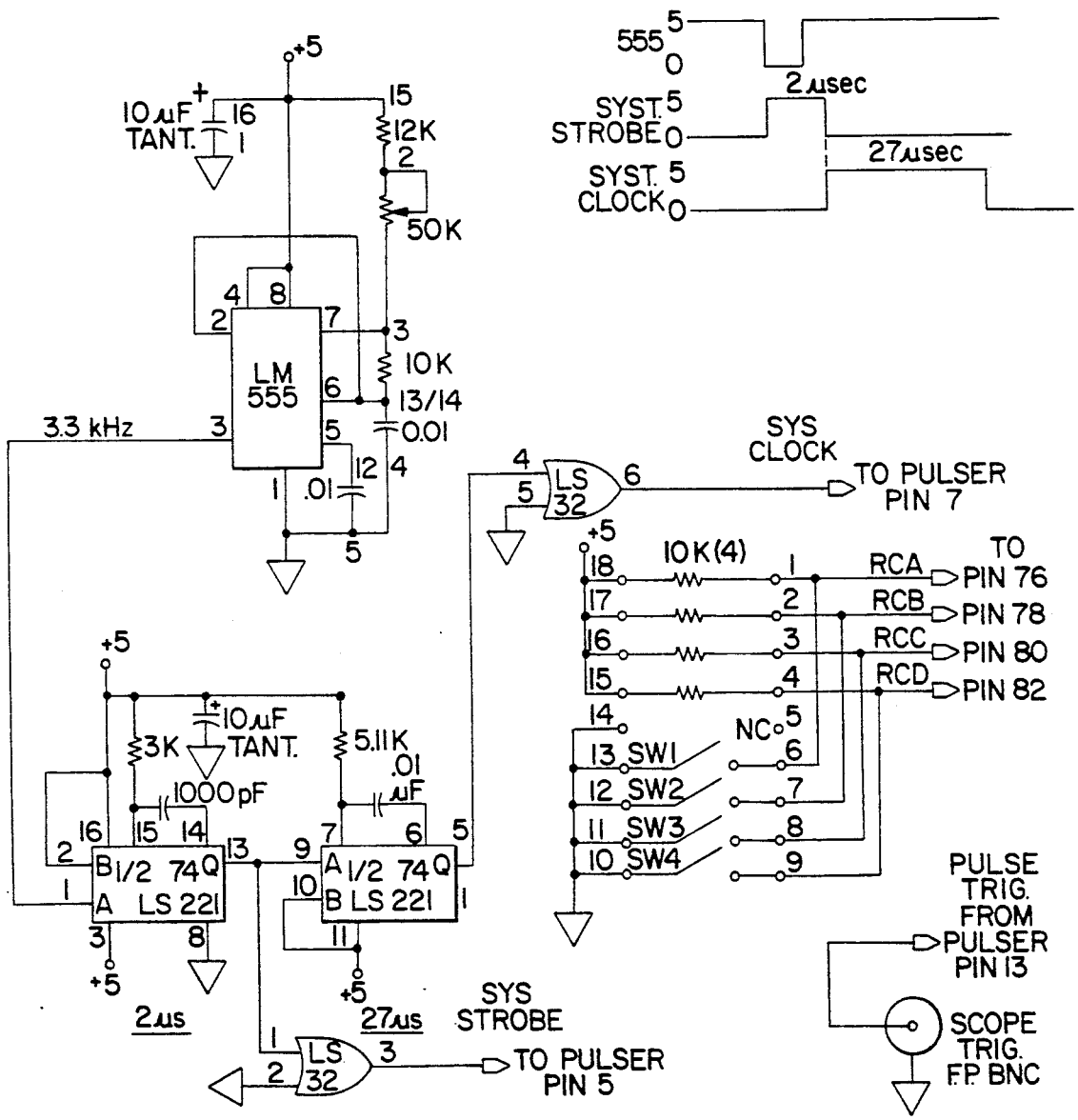
FIG. 5 is a schematic diagram of a pulser interface circuit used in accordance with the present invention.
Figure 6:
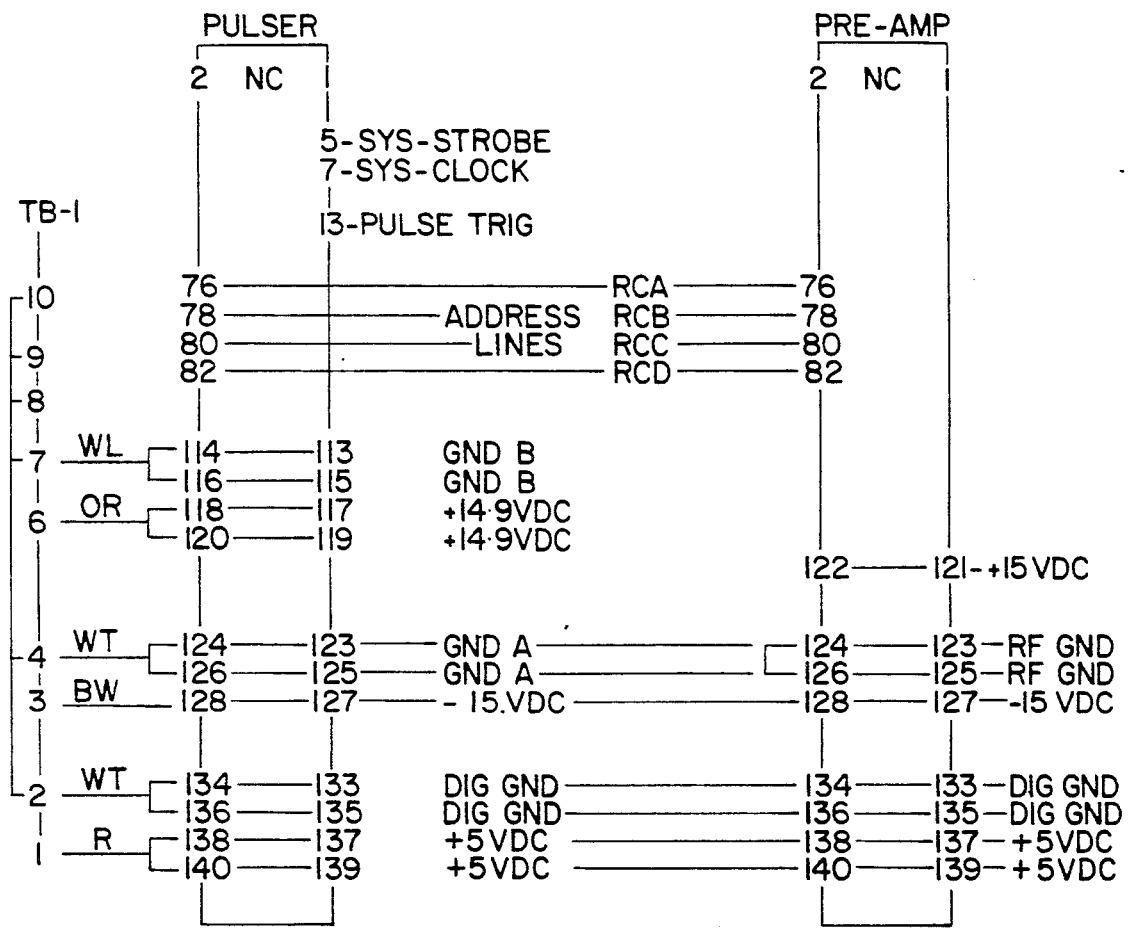
FIG. 6 is a diagram showing the pin connections and voltages for the schematic diagram of FIG. 5.
Figure 7:
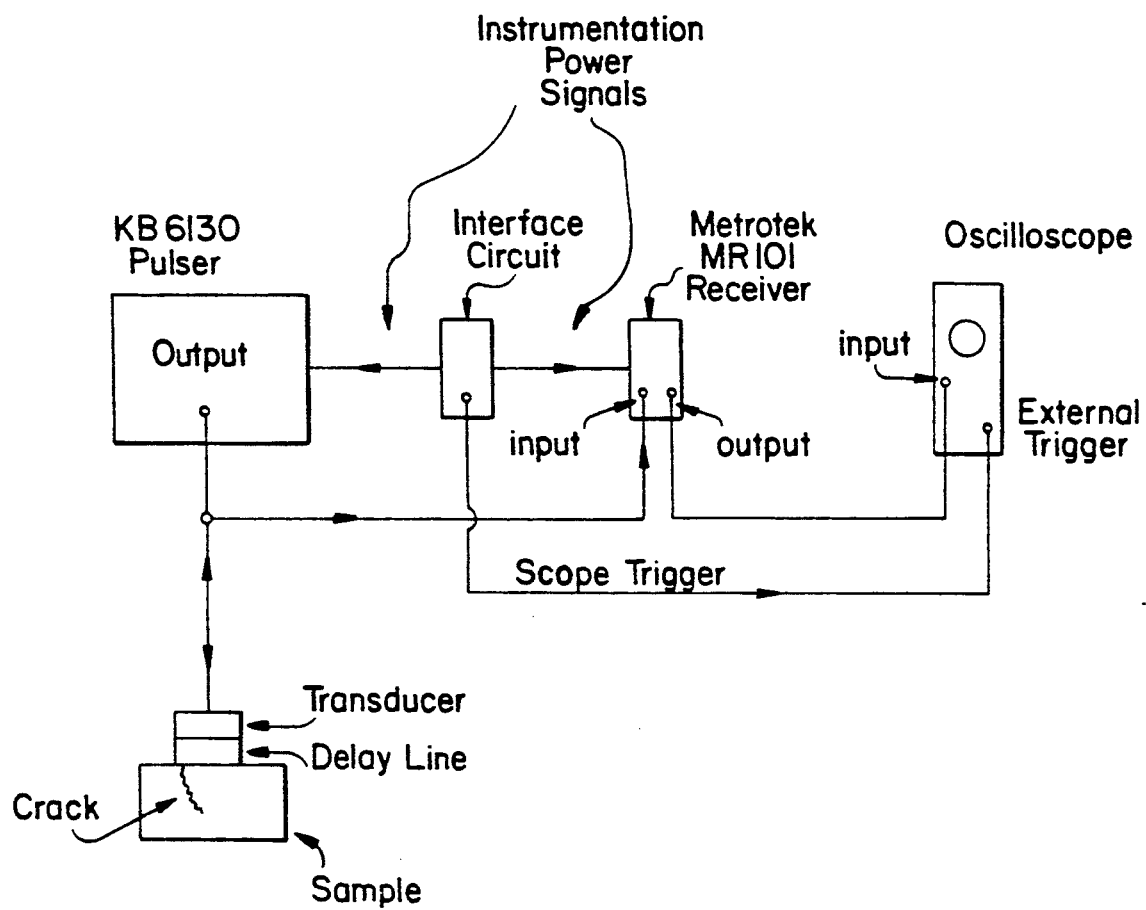
FIG. 7 is a block diagram of the instruments used in accordance with the present invention.

The interface module for the KB-6130 pulser module and the Metrotek MR101 receiver was designed and built for this invention. A schematic diagram of the interface is shown in FIG. 5. The pin connections and voltages for the pulser module are shown in FIG. 6. FIG. 7 is a block diagram of the pulser receiver combination.

Other combinations of pulser receivers may be found that would give comparable results. The invention is not limited to the use of only this equipment.

Figure 4:
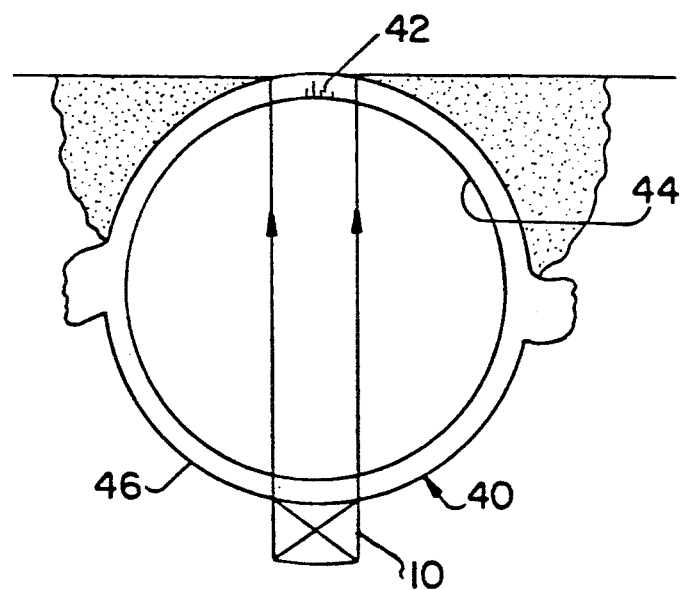
FIG. 4 is a schematic representation, using the apparatus (shown in part) embodied in FIG. 1, illustrating the application of the inventive technique to determine the depth of cracks on the far-side of the inner surface of a tube wall.

As shown by FIG. 4, crack depths can be determined by employing the inventive technique in connection with surfaces that cannot be directly contacted with the transducer. In FIG. 4, the tube 40 has a plurality of surface cracks 42 opening on the inner surface 44 of the tube. A transducer 10 is mounted on the outer surface 46 of the tube at a location diametrically opposite the area in which the cracks 42 are formed. The tube is filled with water and the examination is made by the method previously described. The determination of cracks as shown in FIG. 4 may be employed with particular utility in respect of membrane wall tubes of boiler tubes to determine the depth of cracks resulting from corrosion fatigue cracking such as that which occurs in so-called black liquor recovery boiler tubes in the paper industry.

The inventive technique differs from the vast majority of pulse-echo ultrasonic tests in that it does not use waves that are specularly reflected from a defect. Instead, it relies on the detection of weak, diffracted pulses which are three or more orders of magnitude smaller than reflected signals. In addition, the propagation of the waves along the length of the crack is unique. This approach to determining the depths of surface cracks has a wide variety of potential applications. In particular, it becomes useful in applications where access is limited. As an example, the technique has been used to measure the depth of corrosion fatigue cracks in recovery boilers used in the paper industry. In this application, it is necessary to measure crack depth through the opposite side of a boiler tube that has been filled with water. Other potential applications would include for example the determination of the depths of surface breaking cracks on the outside surface of a pressure vessel In general the technique could potentially apply to any situation where ultrasound can be coupled through the surface where the crack is initiated.

Figure 8:
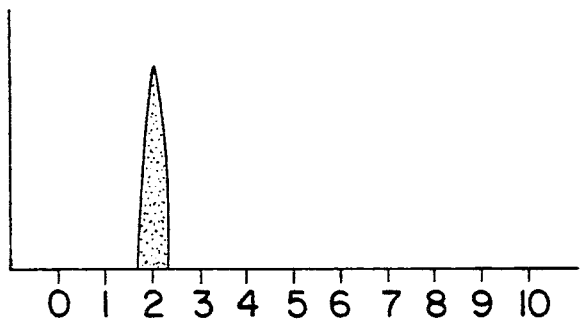
FIG. 8 is a diagram showing a display, such as an oscilloscope, which is displaying a calibration signal used in accordance with the present invention.
Figure 9:
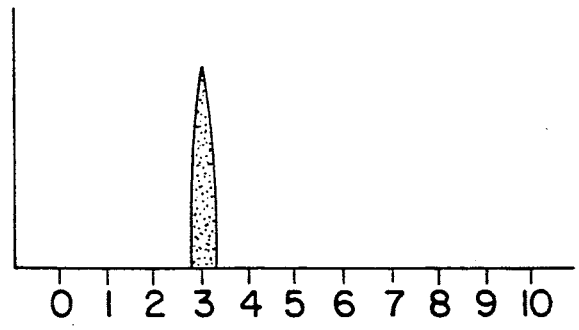
FIG. 9 is a view similar to FIG. 8 showing the signal from a crack having a depth of 75 mils measured in accordance with the inventive technique.

In practice, crack depths are determined by calibrating the horizontal axis of an oscilloscope or ultrasonic instrument to read throughwall depths directly. As an example, consider FIG. 8. If the notch in the calibration standard has a depth of 50 mil, then the calibration setting of the time base of the oscilloscope can be adjusted until the ultrasonic indication from the calibration standard lines up with, for example, the second horizontal mark on the graticule (FIG. 8). As a consequence, the horizontal axis on the ultrasonic scope is now calibrated to read 25 mil of depth per horizontal division. Therefore, for example, if the indication from a crack appears at the third mark on the calibrated screen of the scope (FIG. 9), then the depth of that crack is known to be 75 mils. Calibration is made using a known notch depth (mechanically measured) in a material and shape comparable to the component to be tested.

The present invention uses a pulse-echo technique. In general, pulse-echo implies that the same transducer serves as both the transmitter and receiver. The physical origin of the echo is either diffraction or specular reflection. In the case of specular reflection, the wavefront is redirected according to the laws of geometrical optics. On the other hand, with diffraction, infinitesimal segments of the wavefront interfere constructively to produce the diffracted signal at a given angle.

In the case of diffraction, it should be noted that only the crack tip itself produces the diffracted signal. Therefore, the orientation of the crack itself does not affect the signal. However, in those cases where the crack is not perpendicular to the surface, the measured crack depth will be the projection of the actual crack depth since the time measurement assumes that the crack is perpendicular to the sample's surface.

Also, generally speaking, the diffracted signal is several orders of magnitude smaller than a reflected signal. For the case of electrical discharge machine (EDM) notches, the received signal as observed on the oscilloscope may be as high as 0.5V to 1V, assuming a receiver gain of 40 dB.

In the case of natural flaws, the typical amplitude observed is 0.1V to 0.2V, again, assuming a receiver gain of 40 dB. It should be carefully noted, however, that the amplitude of the signal observed is strongly dependent upon using the maximum pulse excitation voltage with the KB pulser module.

Tests were conducted to prove the operation of the invention. The invention was used to measure a corrosion fatigue crack in a boiler tube. The tube was then subjected to metallographic analysis and the through-wall depth of the crack was determined. There was close agreement of the predicted crack depth and the actual depth, verifying the effectiveness of the inventive technique.

The invention claimed is:

1. A method of ultrasonically determining the depth of a crack in a tube of a known material having a near and a far wall with the crack originating from a root to a tip in the far wall, the far wall being inaccessible for contact with a transducer, comprising the steps of:

mounting an ultrasonic transducer at a location on the near wall of the tube substantially diametrically opposite the root of the crack in the far wall of the tube;

directing longitudinal ultrasonic waves of a known velocity at a predetermined frequency from about 10 to about 50 MHz from the ultrasonic transducer through the near wall into the far wall substantially normal to both walls;

producing a tip diffracted signal at the tip of the crack in the far wall;

receiving the tip diffracted signal propagated from the far wall through the near wall with the ultrasonic transducer situated on the near wall of the tube;

measuring a time from transmission of the longitudinal ultrasonic waves to receipt of the tip diffracted signal; and determining the depth of the crack by correlating said measured time and velocity of the ultrasonic waves for the tube.

2. A method as defined in claim 1, wherein the tube is filled with water.

3. A method as defined in claim 1, wherein the tube is a membrane wall tube.

* * * * *